United States Patent [19]

Meserve

[11] Plant 4,878

[45] Aug. 17, 1982

[54] ILEX PLANT—MESOG VARIETY

[75] Inventor: Kathleen K. Meserve, St. James, N.Y.

[73] Assignee: Conard-Pyle Company, West Grove, Pa.

[21] Appl. No.: 163,069

[22] Filed: Jun. 26, 1980

[51] Int. Cl.[3] ..... A01H 5/00

[52] U.S. Cl. ..... Plt./65

[58] Field of Search ..... Plt./65

*Primary Examiner*—Robert E. Bagwill

*Attorney, Agent, or Firm*—Burns, Doane, Swecker & Mathis

[57] ABSTRACT

A new and distinct variety of Ilex which originated as a cross-pollination of *Ilex rugosa* and *Ilex cornuta* is provided. The new variety possesses attractive medium green foliage, produces an abundance of scarlet berries, and exhibits a compact and symmetrical growth habit and good tolerance to cold and heat.

2 Drawing Figures

SUMMARY OF THE INVENTION

My invention relates to a new, distinctive and useful form of Ilex originated by me by crossing an unnamed and unpatented seedling known botanically as *Ilex rugosa* with an unnamed and unpatented seedling known botanically as *Ilex cornuta.*

The object of my breeding was to create a hardy, compact and versatile shrub which combined the hardiness of *Ilex rugosa* with the beautiful foliage and attractive fruit of *Ilex cornuta.* This object was successfully achieved, and the new variety exhibits a combination of characteristics which distinguish it from all other forms of Ilex of which I am aware.

The following combination of characteristics is exhibited by the new variety:

(a) a well-branched, symmetrical, compact, medium-sized shrub having a vigorous habit of growth which is well-adapted to a wide range of landscape uses, (b) a profusion of dull, scarlet fruit which is produced in spring and which attains its full scarlet coloration in mid to late fall, lasting on the bush into spring of the following year, (c) the ability to be sheared and trimmed to be kept within prescribed limits or shaped to a particular form, (d) cold tolerance which is superior to the species *Ilex cornuta* as well as most cultivars of that species, as evidenced by the fact that the present variety has survived with no visible damage temperatures of −15° F., whereas the species *Ilex cornuta* and most of its cultivars are listed as hardy to 0° F., (e) good heat tolerance which is characteristic of *Ilex cornuta* and which is much improved over *Ilex rugosa,* and, (f) green, semi-glossy to glossy foliage which is less quadrangular in shape as well as less glossy in appearance than *Ilex cornuta.*

In excess of sixty-five percent of two year old container grown plants of the present variety measure approximately 12 to 15 inches in height and breadth when grown at West Grove, Pa. A ten year old plant of the new variety (i.e., the oldest available) has a height of slightly over five feet. At maturity the plant is expected to reach a height in the range of approximately 5 to 7 feet.

Asexual reproduction of my new plant has been accomplished at St. James, N.Y., and at West Grove, Pa. Succeeding propagations have shown that the unique combination of characteristics is fully established and transmitted to successive generations.

The new variety has been named the Mesog variety.

BRIEF DESCRIPTION OF THE PHOTOGRAPHS

The accompanying photographs show typical specimens of my new variety of Ilex as depicted in color as true as is reasonably possible to make the same in color photographs of this character. The specimens in the photographs were grown in the ground at West Grove, Pa.

FIG. 1 shows typical leaves, berries, and unopened flower buds in the spring. The berries were formed during the previous year and have been partially lost from the plant as evidenced by the absence of the abundant berry clusters which earlier were present.

FIG. 2 shows a typical four year old plant of the present variety in mid-fall. Abundant berry clusters are visible. The actual color of the leaves is less blue and more green than depicted.

DETAILED DESCRIPTION

Figure 1:
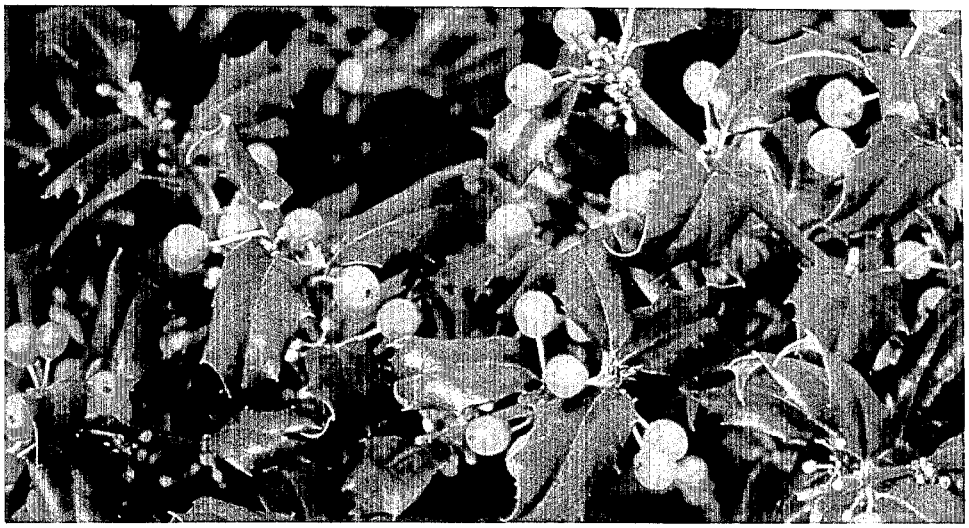
Figure 2:
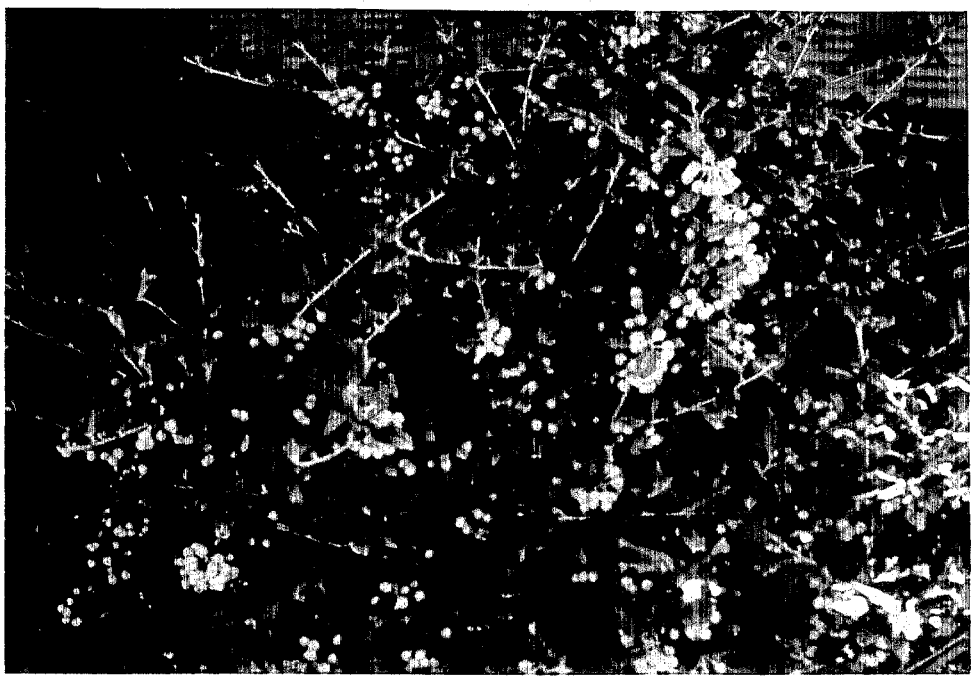

The following is a detailed description of my new variety made in late May from four year old plants growing in the ground at West Grove, Pa. Color terminology is made in accordance with The R.H.S. Colour Chart of The Royal Horticultural Society, London, England.

Parentage: *Ilex rugosa* seedling × *Ilex cornuta* seedling.

Foliage:

*Type.*—Evergreen. Leaves vary from oblong to elliptic, with the larger leaves tending to be oblong, the smaller leaves ovate. Apex acute, base obtuse. Leaf margins spiny, with two to three pairs of prominent spines and a single spine at the apex. The leaf tips are reflexed and twisted unlike the *Ilex rugosa* parent.

*Size.*—Mature leaves on main stem (measurements to tips of spines) — length from approximately 3.1 to 5.4 cm. with an average of approximately 4.6 cm.; width from approximately 2.1 to 3.1 cm., with an average of approximately 2.7 cm. Petiole length from approximately 0.4 cm. to 1.0 cm.

*Color.*—Mature leaves, upper surface — closest to but slightly yellower than Green Group 135A;

under surface — Green Group 143B. Leaves are semi-glossy to glossy.

Fruit:

*Color.*—Dull to semi-glossy, Red Group 44B.

*Size.*—Fairly uniform and substantially round, from approximately 0.7 to 0.9 cm.

*Peduncle.*—The fruit peduncle commonly ranges in length from approximately 0.6 to 1.1 cm., and commonly averages approximately 0.9 cm. in length.

Stems:

*Color.*—Green Group 143B.

Flowers: Flowers are substantially identical to those of *Ilex cornuta.*

I claim:

1. A new and distinct variety of Ilex, substantially as herein shown and described, characterized particularly as to novelty by the unique combination of:

(a) a well-branched, symmetrical, compact, medium-sized shrub having a vigorous habit of growth which is well-adapted to a wide range of landscape uses, (b) a profusion of dull, scarlet fruit which is produced in spring and which attains its full scarlet coloration in mid to late fall, lasting on the bush into spring of the following year, (c) the ability to be sheared and trimmed to be kept within prescribed limits or shaped to a particular form, (d) cold tolerance which is superior to the species *Ilex cornuta* as well as most cultivars of that species, as evidenced by the fact that the present variety has survived with no visible damage temperatures of −15° F., whereas the species *Ilex cornuta* and most of its cultivars are listed as hardy to 0° F., (e) good heat tolerance which is characteristic of *Ilex cornuta* and which is much improved over *Ilex rugosa,* and, (f) green, semi-glossy to glossy foliage which is less quadrangular in shape as well as less glossy in appearance than *Ilex cornuta.*

* * * * *